US008249701B2

(12) United States Patent
Imran et al.

(10) Patent No.: US 8,249,701 B2
(45) Date of Patent: Aug. 21, 2012

(54) METHODS, DEVICES AND SYSTEMS FOR PROGRAMMING NEUROSTIMULATION

(75) Inventors: Mir A. Imran, Los Altos, CA (US); Brian J. Mossop, San Francisco, CA (US); Eyad Kishawi, San Carlos, CA (US)

(73) Assignee: Spinal Modulation, Inc., Menlo Park, CA (US)

( * ) Notice: Subject to any disclaimer, the term of this patent is extended or adjusted under 35 U.S.C. 154(b) by 171 days.

(21) Appl. No.: 12/579,179

(22) Filed: Oct. 14, 2009

(65) Prior Publication Data

US 2010/0121408 A1    May 13, 2010

Related U.S. Application Data

(60) Provisional application No. 61/105,547, filed on Oct. 15, 2008.

(51) Int. Cl.
  *A61N 1/00* (2006.01)
(52) U.S. Cl. .................. 607/2; 607/55; 607/56; 607/57; 607/59; 607/45; 607/46
(58) Field of Classification Search .................... 607/59, 607/2, 45–46, 55–57
   See application file for complete search history.

(56) References Cited

U.S. PATENT DOCUMENTS

| 5,938,690 | A  | 8/1999  | Law et al. |
|---|---|---|---|
| 6,748,276 | B1 | 6/2004  | Daignault, Jr. et al. |
| 7,082,333 | B1 | 7/2006  | Bauhahn et al. |
| 7,146,223 | B1 | 12/2006 | King |
| 7,216,000 | B2 | 5/2007  | Sieracki et al. |
| 7,263,402 | B2 | 8/2007  | Thacker et al. |
| 7,266,412 | B2 | 9/2007  | Stypulkowski |
| 7,295,876 | B1 | 11/2007 | Erickson |
| 7,367,956 | B2 | 5/2008  | King |
| 7,386,348 | B2 | 6/2008  | North et al. |
| 7,463,928 | B2 | 12/2008 | Lee et al. |
| 7,489,970 | B2 | 2/2009  | Lee et al. |
| 7,519,431 | B2 | 4/2009  | Goetz et al. |

(Continued)

OTHER PUBLICATIONS

International Search Report for PCT/US2009/060990, dated Apr. 12, 2010.

*Primary Examiner* — Niketa Patel
*Assistant Examiner* — William Levicky
(74) *Attorney, Agent, or Firm* — Fliesler Meyer LLP (57) ABSTRACT

Methods, devices and systems are provided to efficiently identify, from among a plurality of possible neurostimulation parameter sets, one or more preferred neurostimulation parameter sets that treat a targeted pain of a patient. Each neurostimulation parameter set defines electrode parameters and neurostimulation signal parameters. A plurality of different neurostimulation parameter sets are tested on the patient to thereby identify those tested neurostimulation parameter sets that treat the targeted pain. Each of the tested neurostimulation parameter sets defines an electrode configuration that differs from the other tested neurostimulation parameter sets. All of the tested neurostimulation parameter sets comprise a same value for a specific neurostimulation signal parameter (e.g., pulse width) that if reduced reduces power consumption. If more than one of the tested neurostimulation parameter sets are identified as treating the targeted pain, then neurostimulation parameter sets identified as treating the targeted pain are retested, with the value for the specific neurostimulation signal parameter reduced by a same amount for each of the retested neurostimulation parameter sets, to thereby identify those neurostimulation parameter sets that treat the targeted pain at the reduced power consumption level.

26 Claims, 8 Drawing Sheets

U.S. PATENT DOCUMENTS

| | | |
|---|---|---|
| 7,526,341 B2 | 4/2009 | Goetz et al. |
| 7,542,803 B2 | 6/2009 | Heruth et al. |
| 7,548,786 B2 | 6/2009 | Lee et al. |
| 7,551,960 B2 | 6/2009 | Forsberg et al. |
| 7,571,001 B2 | 8/2009 | Thacker et al. |
| 2002/0116036 A1 | 8/2002 | Daignault, Jr. et al. |
| 2003/0135248 A1 | 7/2003 | Stypulkowski |
| 2003/0204223 A1 | 10/2003 | Leinders et al. |
| 2004/0158298 A1 | 8/2004 | Gliner et al. |
| 2004/0215286 A1 | 10/2004 | Stypulkowski |
| 2005/0060010 A1* | 3/2005 | Goetz ............. 607/48 |
| 2005/0209655 A1 | 9/2005 | Bradley et al. |
| 2005/0215947 A1* | 9/2005 | Heruth et al. ........ 604/66 |
| 2006/0235472 A1* | 10/2006 | Goetz et al. ......... 607/2 |
| 2007/0265678 A1* | 11/2007 | Sieracki et al. ........ 607/46 |

* cited by examiner

METHODS, DEVICES AND SYSTEMS FOR PROGRAMMING NEUROSTIMULATION

PRIORITY CLAIM

This application claims priority under 35 U.S.C. 119(e) to U.S. Provisional Patent Application No. 61/105,547, entitled "Patient Programmable Stimulator System", filed Oct. 15, 2008, which is incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

Embodiments of the present invention relate to methods, devices and systems that provide neurostimulation to treat pain.

BACKGROUND OF THE INVENTION

Approved by the FDA in 1989, spinal cord stimulation (SCS) has become a standard treatment for patients with chronic pain in their back and/or limbs who have not found pain relief from other treatments. In general, neurostimulation works by applying an electrical current to nerve tissue in the pathway of the chronic pain. This creates a pleasant sensation that blocks the brain's ability to sense the previously perceived pain. There are two conventional forms of electrical stimulation commonly used to treat chronic pain: Spinal Cord Stimulation (SCS) and Peripheral Nerve Field Stimulation (PNFS). In spinal cord stimulation, electrical leads are placed onto the spinal column. A programmable pulse generator is implanted in the upper buttock or abdomen (under the skin) which emits electrical currents to the spinal column. Peripheral nerve field stimulation is similar to spinal cord stimulation, however peripheral nerve field stimulation involves placing the leads just under the skin in an area near to the nerves involved in pain.

In both approaches, the implantable pulse generator (IPG) can be programmed with the use of an external programmer. Such programming currently requires the interaction of two individuals: the programming person and the patient. The programming person is typically a company representative of the IPG manufacturer or a member of the clinical staff. The programming person manually adjusts the various stimulus parameters with the use of the external programmer. The patient gives feedback to the programming person as the person cycles through the parameters. Thus, after every parameter change made by the programming person, they must ask the patient for efficacy feedback. This use of personnel is expensive and time consuming, particularly for clinical staff who currently do not have insurance reimbursement codes for such tasks.

Efforts to reduce programming time have been made by preparing pre-made program stimulation "sets" (i.e. pre-defined amplitude, pulse width, repetition rate, etc). The stimulation sets are then presented to the patient in a randomized order. The patient responds to each set regarding its efficacy. After the patient feedback has been collected, the data is presented to the physician who makes the decision as to which stimulation set to assign to the patient. However, this methodology reduces the programming options to a very small subset of the possible parameter combinations. The likelihood of the patient's pain profile matching a premade set is relatively low.

Thus, it is desired to provide devices, systems and methods which allow individualized programming of a stimulator for a given patient while reducing and preferably minimizing time and cost. Such devices, systems and methods should improve and preferably optimize the programming parameters while more fully utilizing the capabilities of the stimulator. At least some of these objectives will be met by embodiments of the present invention.

SUMMARY OF THE INVENTION

Methods, devices and systems are provided to efficiently identify, from among a plurality of possible neurostimulation parameter sets, one or more preferred neurostimulation parameter sets that treat a targeted pain of a patient. Each such neurostimulation parameter set defines electrode parameters and neurostimulation signal parameters. The electrode parameters of each neurostimulation parameter set can define which electrodes are used to provide neurostimulation. Additionally, the electrode parameters of each neurostimulation parameter set can define which one or more electrodes used to provide neurostimulation are connected as a cathode, and which one or more electrodes used to provide neurostimulation are connected as an anode. The neurostimulation signal parameters of each neurostimulation parameter set can define a value for each of pulse width, pulse amplitude and pulse repetition rate, but are not limited thereto.

In accordance with an embodiment, a plurality of different neurostimulation parameter sets are tested on the patient to thereby identify those tested neurostimulation parameter sets that treat the targeted pain. Each of the tested neurostimulation parameter sets defines an electrode configuration that differs from the other tested neurostimulation parameter sets, and all of the tested neurostimulation parameter sets comprise a same value for a specific neurostimulation signal parameter (e.g., pulse width) that if altered or changed reduces power consumption. In some embodiments, if more than one neurostimulation parameter set that treats the targeted pain is identified, then the neurostimulation parameter sets identified as treating the targeted pain are retested, with the value for the specific neurostimulation signal parameter (e.g., pulse width) reduced by a same amount for each of the retested neurostimulation parameter sets, to thereby identify those neurostimulation parameter sets that treat the targeted pain at the reduced power consumption level.

In accordance with an embodiment, if the retesting identifies more than one neurostimulation parameter set that treats the targeted pain, then the retesting can be repeated until only one neurostimulation parameter set that treats the targeted pain is identified. Each time the retesting is repeated the value for the specific neurostimulation signal parameter is again reduced. In accordance with an embodiment, the amount by which the value for the specific neurostimulation signal parameter is reduced stays the same or decreases. In accordance with an embodiment, the amount by which the value of the specific neurostimulation signal parameter is reduced for each of the retested neurostimulation parameter sets is dependent upon the number of neurostimulation parameter sets being retested. For example, the amount the value is reduced can be proportional to the number of neurostimulation parameter sets being retested. More generally, the greater the number of neurostimulation parameter sets being retested the greater the amount by which the value of the specific neurostimulation signal parameter is reduced The specific neurostimulation signal parameter referred to above (that has its value reduced or increased) can be, e.g., pulse width, pulse amplitude or pulse repetition rate, but is not limited thereto.

In accordance with an embodiment, if none of the neurostimulation parameter sets tested treat the targeted pain, then the plurality of neurostimulation parameter sets can be retested with a value for the specific neurostimulation signal parameter (e.g., pulse width) or another neurostimulation parameter (e.g., pulse amplitude) increased by a same amount for each of the retested neurostimulation parameter sets, to thereby identify those neurostimulation parameter sets that treat the targeted pain with the increased value.

Specific embodiments of the present invention are directed to an external programmer that is configured to efficiently identify, from among a plurality of possible neurostimulation parameter sets, one or more preferred neurostimulation parameter sets that treat a targeted pain of a patient. Each neurostimulation parameter set defines electrode parameters and neurostimulation signal parameters. In an embodiment the external programmer is a patient programmer. In another embodiment, the external programmer is a clinician programmer. Either way, the external programmer includes a controller, a user interface, memory and a telemetry circuit. A plurality of different neurostimulation parameter sets to be tested on the patient are stored in the memory, wherein all of the neurostimulation parameter sets to be tested comprise a same value for a specific neurostimulation signal parameter that if reduced reduces power consumption. Such sets can be predefined, generated by the controller, or generated by a clinician or physician. The controller is configured to provide test instructions that instruct an implantable pulse generator (IPG), implanted within the patient, to test on the patient the plurality of different neurostimulation parameter sets. The telemetry circuitry is configured to transmit the test instructions to the IPG implanted within the patient. The user interface is configured to accept feedback that identifies those tested neurostimulation parameter sets that treat the targeted pain.

In accordance with an embodiment, the controller is configured to provide retest instructions, in response to more than one of the tested neurostimulation parameter sets being identified as treating the targeted pain. Here the retest instructions instruct the IPG to retest on the patient the neurostimulation parameter sets identified as treating the targeted pain, with the value for the specific neurostimulation signal parameter reduced by a same amount for each of the retested neurostimulation parameter sets. The telemetry circuit is also configured to transmit the retest instructions to the IPG. The user interface is also configured to accept feedback that identifies those retested neurostimulation parameter sets that treat the targeted pain at the reduced power consumption level.

In accordance with an embodiment, the controller is configured to repeatedly provide retest instructions, in response to more than one of the retested neurostimulation parameter sets being identified as treating the targeted pain. Each time the controller provides such retest instructions, the value for the specific neurostimulation signal parameter is again reduced. Each time the controller provides such retest instructions, the amount by which the value for the specific neurostimulation signal parameter is reduced stays the same or decreases. In accordance with an embodiment, the amount by which the value is reduced is dependent upon the number of neurostimulation parameter sets being retested. For example, the amount by which the value of is reduced can be proportional to the number of neurostimulation parameter sets being retested. More generally, the greater the number of neurostimulation parameter sets being retested the greater the amount by which the value of the specific neurostimulation signal parameter is reduced In accordance with an embodiment, the controller is configured to provide retest instructions, in response to none of the tested neurostimulation parameter sets being identified as treating the targeted pain. Here the retest instructions instruct the IPG to retest on the patient the plurality of neurostimulation parameter sets, with a value for the specific neurostimulation signal parameter or another neurostimulation parameter increased by a same amount for each of the retested neurostimulation parameter sets.

In accordance with specific embodiments, the neurostimulation parameter sets comprise dorsal root ganglion (DRG) neurostimulation parameter sets for DRG stimulation of the patient.

This summary is not intended to summarize all of the embodiments of the present invention. Further and alternative embodiments, and the features, aspects, and advantages of the embodiments of invention will become more apparent from the detailed description set forth below, the drawings and the claims.

DETAILED DESCRIPTION OF THE INVENTION

Devices, systems and methods are provided to allow programming of an IPG (also referred to as a stimulator) by a patient, clinician and/or physician, or other programming person thereby maximizing the available stimulation parameters, saving time and cost, and optimizing the treatment for the most beneficial outcome. Programming is achieved with the use of an external programmer of the present invention which communicates with the implanted stimulator. The external programmer varies the stimulation parameters according to a programming protocol which prompts the patient for efficacy feedback. The protocol utilizes the feedback in an iterative process which determines the optimum parameter settings for the individual patient. Such use of an external programmer can significantly reduce or eliminate the need for a skilled programming person (e.g., a clinician or physician) to cycle through various parameters which is limited by time, cost, patience and skill. Nevertheless, a clinician or physician can still participate in the protocols disclosed herein, and likely will.

The external programmer of an embodiment of the present invention may be used to program a variety of stimulators. Although the examples described herein are related to nerve stimulation, particularly dorsal root stimulation and/or dorsal root ganglion stimulation, the invention is applicable to a variety of other applications which involve patient feedback for programming.

Nerve stimulation may be achieved with the use of a variety of stimulators. In some embodiments, the stimulator comprises electronic circuitry, optionally enclosed in a housing, which may be implanted subcutaneously and electronic leads that are coupled to the electronic circuitry. The leads include stimulating electrodes that are electrically couplable to the nerve anatomy. In some embodiments, the electronic circuitry includes a processor and memory which are used to provide the appropriate stimulation signals to the electrodes. Typically, the electronic circuitry of the stimulator also includes a telemetry circuit for communication with separate devices, of which one may be for programming the stimulator's various operational parameters. It may be appreciated that memory may alternatively or additionally be located on the separate device, as will be explained in more detail below.

Figure 1A:
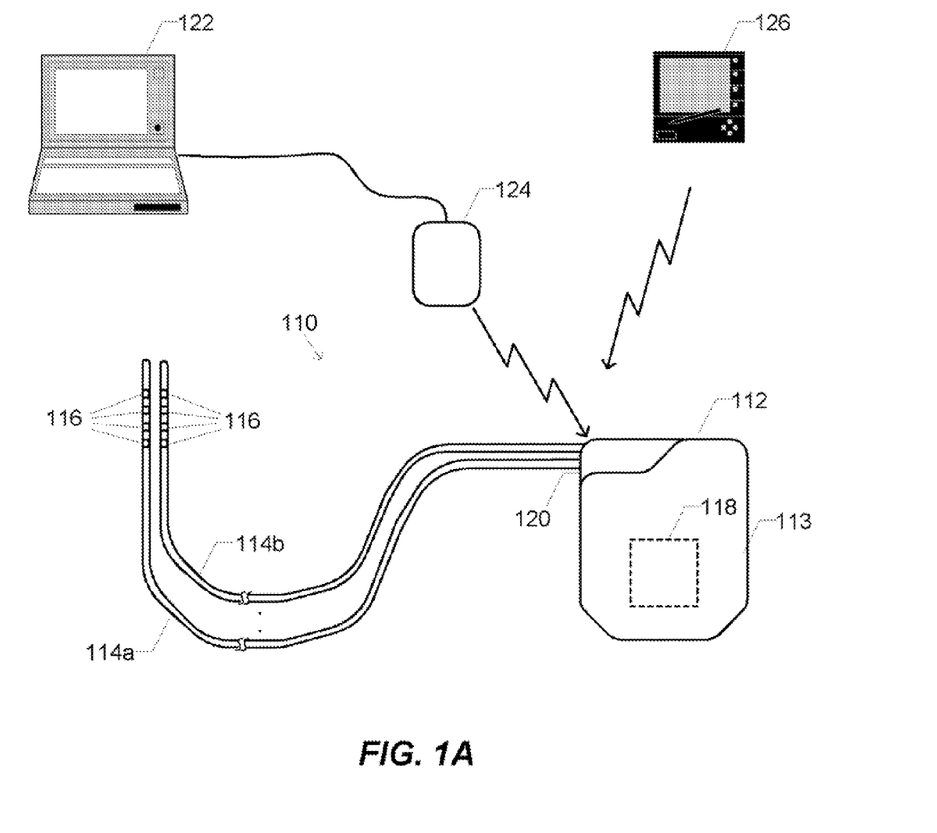
FIG. 1A illustrates an example stimulation system of an embodiment of the present invention.

An example stimulation system 110 of an embodiment of the present invention is illustrated in FIG. 1A. In this embodiment, the system 110 includes an implantable pulse generator (IPG) 112, which is implantable in a subcutaneous pocket within a patient's body, and one or more leads 114 each having at least one electrode 116. While two leads 114 are shown in FIG. 1A (labeled 114a and 114b), more or less leads can be used. While the electrodes 116 are shown in particular configurations and locations, numerous alternative electrode configurations and positions are contemplated. The IPG 112 includes electronic circuitry 118 contained therein. The at least one electrode 116 is electrically coupled to the electronic circuitry 118 by coupling the lead 114 to a connector 120 of the IPG 112. Where a housing 113 (also referred to as the "case" or "can") of the IPG 112 is electrically conductive, the housing 113 can act as an electrode, as explained in more detail below.

The electronic circuitry 118 is configured to provide an electrically stimulating signal (also referred to a neurostimulation signal) to a nerve tissue via the electrode(s) 116. An external computer or programmer 122 is used to program various stimulation parameters and/or other instructions into the electronic circuitry 118. The programmer 122 includes a processor (or other type of controller) and a memory device having one or more code modules. The processor or other controller executes the one or more code modules to perform programming of the IPG 112 based on feedback from the patient during a programming protocol. For example, the external programmer can transmit instructions to the IPG that instruct the IPG to test specific neurostimulation parameter sets, adjust certain parameters of the sets, and/or program certain set(s) as those to be used by the IPG for chronic treatment of pain. As shown in FIG. 1A, the external programmer 122 may be coupled to a telemetry device 124 that communicates with the electronic circuitry 118 via radio frequency or other wireless signals. However, it may be appreciated that the telemetry device 124 may be included within the programmer 122. Regardless whether the telemetry device is within the programmer 122 or coupled to the programmer 122, the programmer can be said to include telemetry circuitry.

In the embodiment of FIG. 1A, the circuitry 118, the telemetry device 124, and the external programmer 122 are included in a data processing system of a stimulation system. Generally, the data processing system included in embodiments of the invention may include at least one processor (or other controller), which will typically include circuitry implanted in the patient, circuitry external of the patient, or both. When external processor circuitry is included in the data processing system, it may include one or more proprietary processor boards, and/or may make use of a general purpose desktop computer, notebook computer, handheld computer, or the like. The external processor may communicate with a number of peripheral devices (and/or other processors) via a bus subsystem, and these peripheral devices may include a data and/or programming storage subsystem or memory. The peripheral devices may also include one or more user interface input devices, user interface output devices, and a network interface subsystem to provide an interface with other processing systems and networks such as the Internet, an intranet, an Ethernet™, and/or the like. Implanted circuitry of the processor system may have some or all of the constituent components described above for external circuitry, with peripheral devices that provide user input, user output, and networking generally employing wireless communication capabilities, although hard-wired embodiments or other trans-cutaneous telemetry techniques could also be employed.

An external or implanted memory of the processor system can be used to store, in a tangible storage media, machine readable instructions or programming in the form of a computer executable code embodying one or more of the methods described herein. The memory may also similarly store data for implementing one or more of these methods. The memory may, for example, include a random access memory (RAM) for storage of instructions and data during program execution, and/or a read only memory (ROM) in which fixed instructions are stored. Persistent (non-volatile) storage may be provided, and/or the memory may include a hard disk drive, a compact digital read only memory (CD-ROM) drive, an optical drive, DVD, CD-R, CD-RW, solid-state removable memory, and/or other fixed or removable media cartridges or disks. Some or all of the stored programming code may be altered after implantation and/or initial use of the device to alter functionality of the stimulator system.

The functions and methods described herein may be implemented with a wide variety of hardware, software, firmware, combinations thereof, and/or the like. In many embodiments, the various functions can be implemented by modules, with each module comprising data processing hardware and/or software configured to perform the associated function. The modules may all be integrated together so that a single processor board runs a single integrated code, but will often be separated so that, for example, more than one processor board or chip or a series subroutines or codes are used. Similarly, a single functional module may be separated into separate subroutines or be run in part on a separate processor chip that is integrated with another module. Hence, a wide variety of centralized or distributed data processing architectures and/or program code architectures may be employed within different embodiments.

As described in more detail below, the electronic circuitry can comprise and/or is included within a controller (e.g., processor) for controlling the operations of the device, including stimulating, signal transmission, charging and/or using energy from a battery device for powering the various components of the circuit, and the like. As such, the processor and battery device can be coupled to each of the major components of the implanted circuit. It is also possible that the battery is coupled to a voltage regulator that produces the various voltage levels that power components of the electronic circuitry.

The external programmer 122 includes a plurality of code modules for execution by a processor. The code modules are executed to determine a variety of parameters, such as electrode choice or combination and stimulation signal amplitude, pulse width and repetition rate which are optimal for pain management of the individual patient at that time. The code modules utilize input from the patient in determining the parameters. Therefore, the code modules are executed while the system 110 is implanted in the patient.

As mentioned, one of the determined parameters is electrode choice or combination. In some instances, the lead 114 will be positioned on or near nerve tissue in a manner wherein fewer than all of the electrodes 116 are optimally placed to desirably stimulate the nerve tissue. In some embodiments, the lead 114 is positioned on or near a dorsal root ganglion and the electrodes 116 are disposed at varying locations in relation to the dorsal root ganglion. Desirability of stimulation by each of the electrodes 116 is typically based on its location in relation to the dorsal root ganglion in combination with the neurostimulation signal parameters. It is desired to provide stimulation energy to the one or more electrodes 116 of a lead 114 that is/are optimally placed and to provide no stimulation energy to the one or more electrodes 116 which is/are not optimally placed. This conserves energy use and decreases the incidence of undesired stimulation of surrounding tissue. In some instances, only one electrode 116 will provide stimulation out of possibly four, six, eight or more electrodes 116. In other instances, a particular combination of electrodes 116 will provide the desired stimulation. Therefore, it is desired to determine which of the electrodes 116 are most desirably positioned within the anatomy for a particular treatment outcome.

The external programmer 122 discussed above can be a clinician programmer or a patient programmer, but hereafter is assumed to be a clinician programmer that a patient does not take home with them. Accordingly, a separate external patient programmer 126 is also shown in FIG. 1A, which can be configured to implement all of or some of the same functions as the clinician programmer 122, and can also be configured to implement patient specific functions, some examples of which are described below.

Figure 1B:
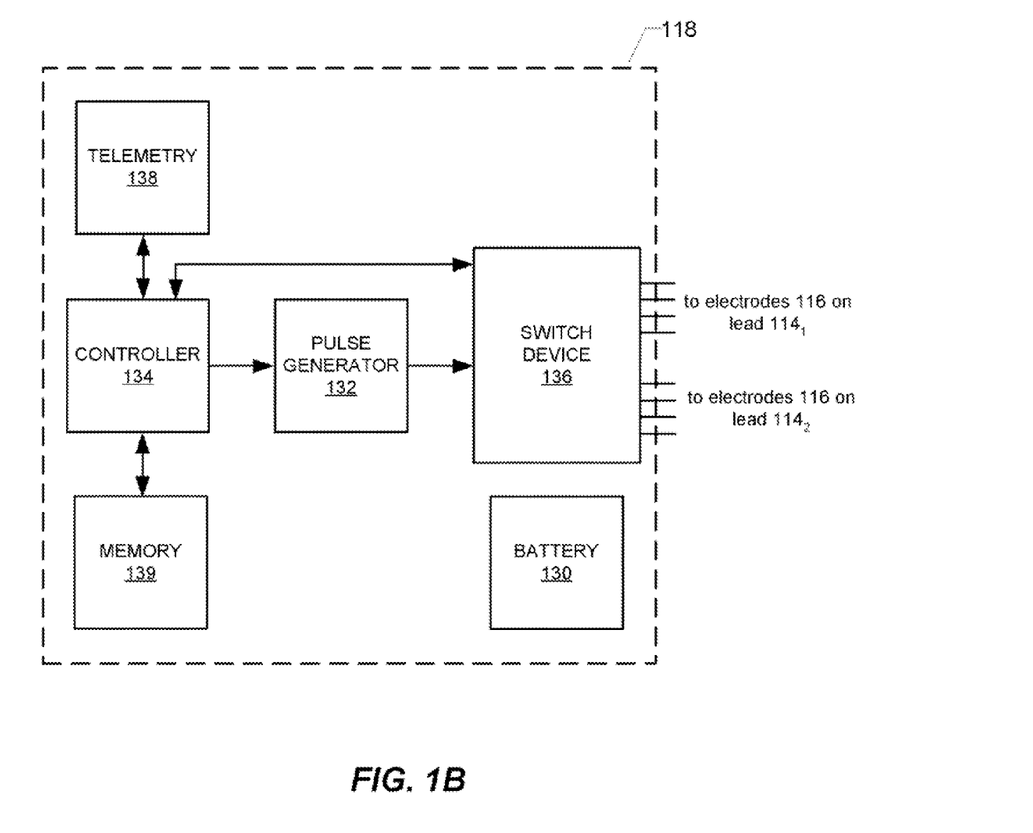
FIG. 1B is a simplified block diagram that illustrates possible components of the electronic circuitry of the implantable pulse generator (IPG) shown in FIG. 1A.

FIG. 1B is a simplified block diagram that illustrates possible components of the electronic circuitry 118 of the IPG 112 shown in FIG. 1A. Referring to FIG. 1B, the electronic circuitry 118 is shown as including a battery 130, a pulse generator 132, a controller 134, a switch device 136, telemetry circuitry 138 and memory 139.

The battery 130 can be used to power the various other components of the electronic circuitry 118. Further, the battery 130 can be used to generate stimulation pulses. As such, the battery can be coupled to the pulse generator 132, the controller 134, the switch device 136, the telemetry circuitry 138 and the memory 139. A voltage regulator (not shown) can step up or step down a voltage provide by the battery 130 to produce one or more predetermined voltages useful for powering such components of the electronic circuitry 118. Additional electronic circuitry, such as capacitors, resistors, transistors, and the like, can be used to generate stimulation pulses, as is well known in the art.

The pulse generator 132 can be coupled to electrodes 116 of the lead(s) 114 via the switch device 136. The pulse generator 132 can be a single- or multi-channel pulse generator, and can be capable of delivering a single stimulation pulse or multiple stimulation pulses at a given time via a single electrode combination or multiple stimulation pulses at a given time via multiple electrode combinations. In an embodiment the pulse generator 132 and the switch device 136 can be configured to deliver stimulation pulses to multiple channels on a time-interleaved basis, in which case the switch device 136 can time division multiplex the output of pulse generator 132 across different electrode combinations at different times to deliver multiple programs or channels of stimulation energy to the patient.

The controller 134 can control the pulse generator 132 to generate stimulation pulses, and control the switch device 136 to couple the stimulation energy to selected electrodes. More specifically, the controller 134 can control the pulse generator 132 and the switch device 136 to deliver stimulation energy in accordance with parameters specified by one or more neurostimulation parameter sets stored within the memory 139. Exemplary programmable parameters that can be specified include the pulse amplitude, pulse width, and pulse rate (also known as repetition rate or frequency) for a stimulation waveform (also known as a stimulation signal). Additionally, the controller 134 can control the switch device 136 to select different electrode configurations for delivery of stimulation energy from the pulse generator 132. In other words, additional programmable parameters that can be specified include which electrodes 116 of which lead(s) 114 are to be used for delivering stimulation energy and the polarities of the selected electrodes 116. Each electrode 116 can be connected as an anode (having a positive polarity), a cathode (having a negative polarity), or a neutral electrode (in which case the electrode is not used for delivering stimulation energy, i.e., is inactive). A set of parameters can be referred to as a neurostimulation parameter set since they define the neurostimulation therapy to be delivered to a patient. One neurostimulation parameter set may be useful for treating pain in one location of the body of the patient, while a second neurostimulation parameter set may be useful for treating pain in a second location.

The controller 134 can include a microprocessor, a microcontroller, a digital signal processor (DSP), an application specific integrated circuit (ASIC), a field-programmable gate array (FPGA), a state machine, or similar discrete and/or integrated logic circuitry. The switch device 136 can include a switch array, switch matrix, multiplexer, and/or any other type of switching device suitable to selectively couple stimulation energy to selected electrodes. The memory 139 can include RAM, ROM, NVRAM, EEPROM or flash memory, but is not limited thereto. Various programs and/or neurostimulation parameter sets can be stored in the memory 139, examples of which are discussed herein.

Once a neurostimulation parameter set is determined by the external programmer 122, the IPG 112 can be programmed with the parameters of the set. The appropriate electrode(s) 116 on the lead 114 then stimulate the nerve tissue with the determined neurostimulation signal.

Figure 1C:
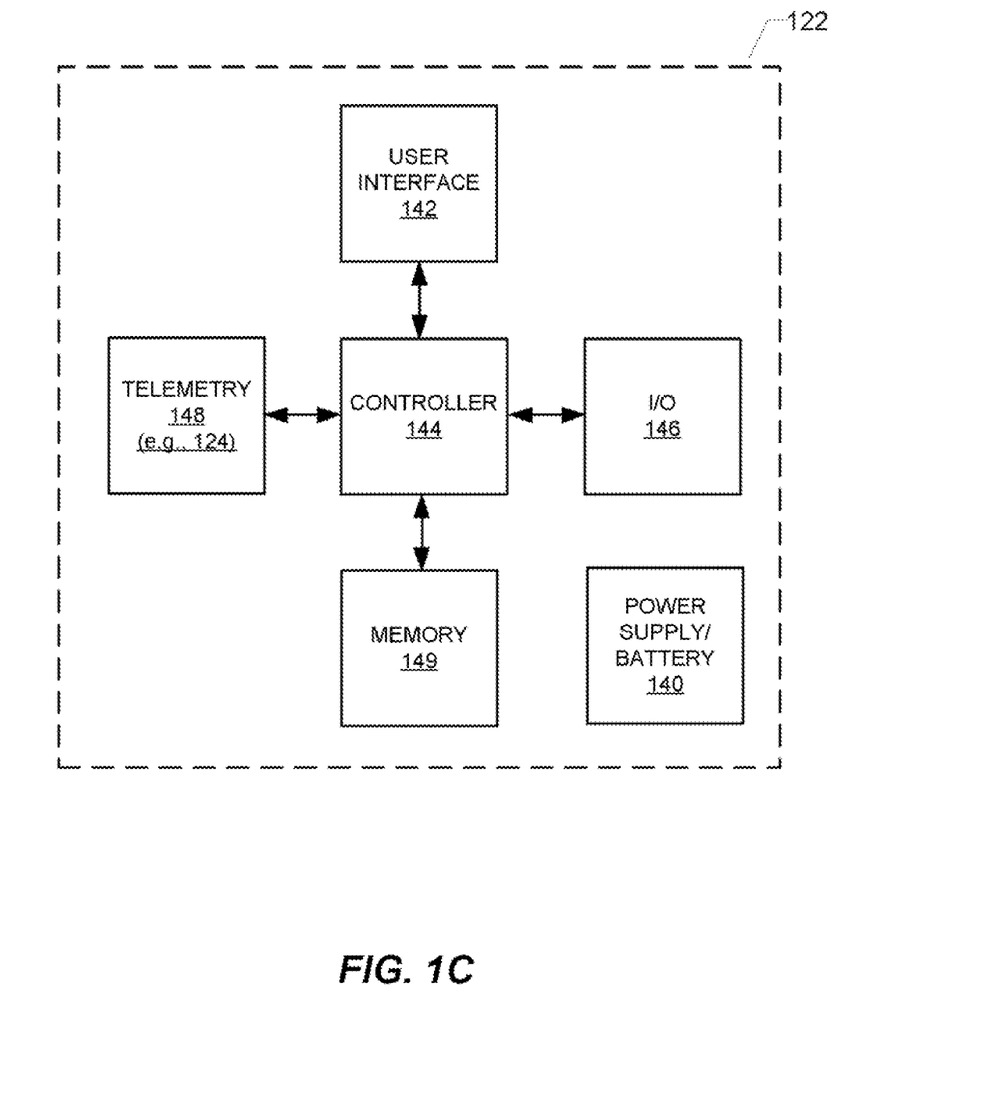
FIG. 1C is a simplified block diagram that illustrates possible components of the clinical external programmer shown in FIG. 1A.

FIG. 1C is a simplified block diagram that illustrates possible components of the external programmer 122 shown in FIG. 1A, which can be used, e.g., as a clinician programmer. Referring to FIG. 1C, the external programmer 122 is shown as including a power supply 140, a user interface 142, a controller 144, input and output (I/O) circuitry 146, telemetry circuitry 148 and memory 149.

The power supply 140, which can include a battery, can be used to power the various other components of the external programmer 122. As such, the power supply 140 can be coupled to the user interface 142, the controller 144, the input and output (I/O) circuitry 146, the telemetry circuitry 148 and the memory 149. A voltage regulator (not shown) can step up or step down a voltage provide by a battery or an external power source to produce one or more predetermined voltages useful for powering such components of the external programmer 122.

A clinician or physician may interact with the controller 144 via the user interface 142 in order to test various neurostimulation parameter sets, input user feedback, select preferred or optimal programs, and the like. The user interface 142 can include a display, a keypad, a touch screen, one or more peripheral pointing devices (e.g., a mouse, touchpad, joystick, trackball, etc.), and the like. The controller 144 can provide a graphical user interface (GUI) via the user interface 142 to facilitate interaction with a clinician or physician. The controller 144 can include a microprocessor, a microcontroller, a digital signal processor (DSP), an application specific integrated circuit (ASIC), a field-programmable gate array (FPGA), a state machine, or similar discrete and/or integrated logic circuitry. The I/O circuitry 146 can include transceivers for wireless communication, ports for wired communication and/or communication via removable electrical media, and/or appropriate drives for communication via removable magnetic or optical media. The telemetry circuitry 148 can be the telemetry circuitry 124 described above with reference to FIG. 1A, or separate but similar telemetry circuitry.

As described in addition detail below, the controller 144 can collect information relating to tested electrode parameters (e.g., combinations) and neurostimulation signal parameters, and store the information in the memory 149 for later retrieval and review by a clinician, physician or by the controller 144 to facilitate identification of one or more preferred neurostimulation parameter sets. The controller 144 can send instructions to the IPG 112 via the telemetry circuit 148 to cause the testing of various neurostimulation parameter sets. For example, the controller 144 can effectuate the testing of neurostimulation parameter sets created by the controller 144, a clinician or a physician to the IPG 112.

The memory 149 can include program instructions that, when executed by the controller 144, cause the programmer 122 to perform at least some of the functions described herein. For example, the controller 144 can execute program instructions that specify protocols for testing various neurostimulation parameter sets and selecting one or more preferred neurostimulation parameter sets. The memory 149 can also store one or more neurostimulation parameter sets determined to treat targeted pain for a patient, along with information about the patient. The memory 149 can include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

Figure 1D:
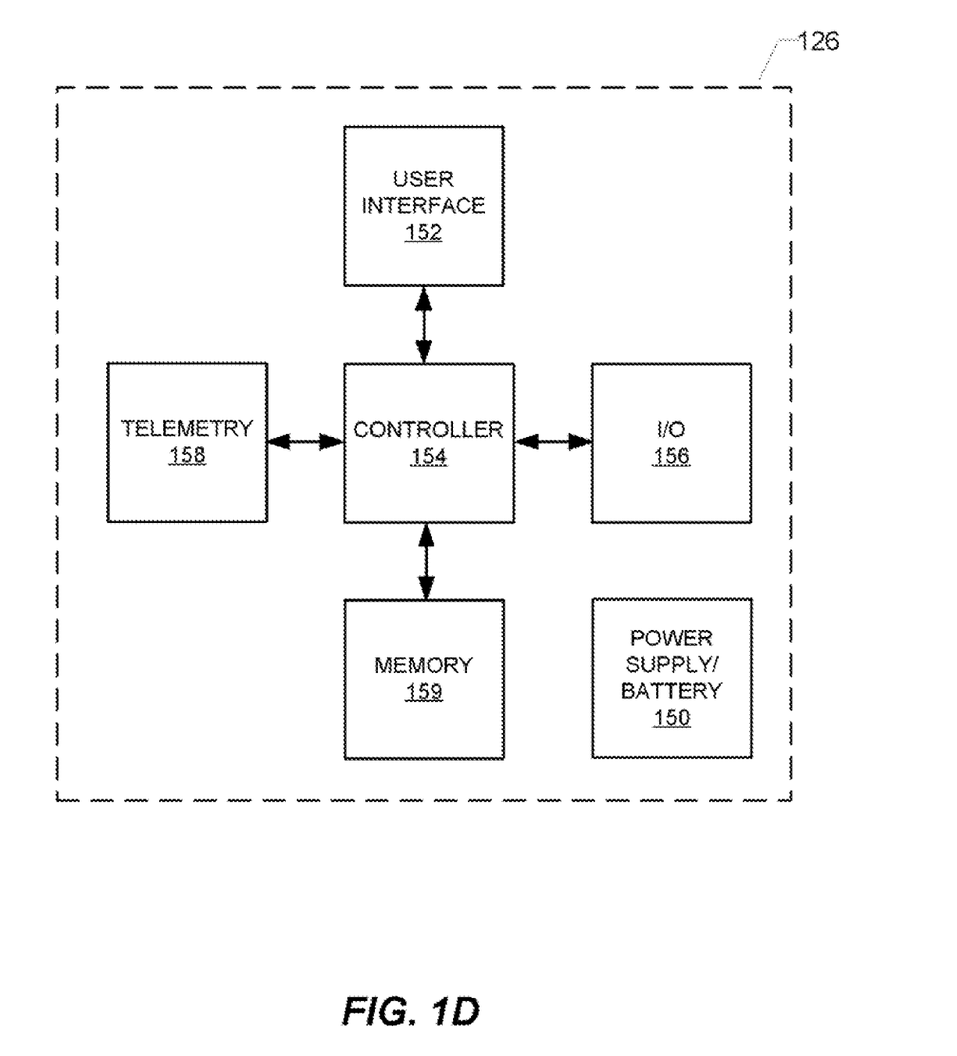
FIG. 1D is a simplified block diagram that illustrates possible components of the patient programmer shown in FIG. 1A.

FIG. 1D is a simplified block diagram that illustrates possible components of the patient programmer 126 shown in FIG. 1A. Referring to FIG. 1D, the patient programmer is shown as including a power supply 150, a user interface 152, a controller 154, input and output (I/O) circuitry 156, telemetry circuitry 158 and memory 159. The power supply 150, which can include a battery, can be used to power the various other components of the patient programmer 126. As such, the power supply 150 can be coupled to the user interface 152, the controller 154, the input and output (I/O) circuitry 156, the telemetry circuitry 158 and the memory 159. A voltage regulator (not shown) can step up or step down a voltage provide by a battery or an external power source to produce one or more predetermined voltages useful for powering such components of the patient programmer 126.

A patient can interact with the controller 154 via the user interface 152 in order to select, modify or otherwise control delivery of neurostimulation therapy. For example, the patient may be able to select among various neurostimulation parameter sets that are stored in the memory 159. Additionally, or alternatively, the patient may be able to increase or decrease specific neurostimulation signal parameters, such as amplitude, to tailor the therapy to the pain being experienced at the time. The user interface 142 can include a display, a keypad, a touch screen, one or more peripheral pointing devices (e.g., a mouse, touchpad, joystick, trackball, etc.), and the like. The controller 154 can provide a graphical user interface (GUI) via the user interface 152 to facilitate interaction with a patient. The controller 154 can include a microprocessor, a microcontroller, a digital signal processor (DSP), an application specific integrated circuit (ASIC), a field-programmable gate array (FPGA), a state machine, or similar discrete and/or integrated logic circuitry. The I/O circuitry 146 can include transceivers for wireless communication, ports for wired communication and/or communication via removable electrical media, and/or appropriate drives for communication via removable magnetic or optical media.

In some embodiments, the memory 159 can store data related to neurostimulation parameter sets that are available to be selected by the patient for delivery of neurostimulation therapy to the patient using the IPG 112 implanted within the patient. In some embodiments, the controller 154 can record usage information and store usage information in the memory 159. The memory 159 can include program instructions that, when executed by the controller 154, cause the patient programmer 126 to perform functions ascribed to the patient programmer 126. The memory 159 can include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

The telemetry circuitry 158 allows the controller to communicate with IPG 112, and the input/output circuitry 156 allows the controller 154 to communicate with the clinician external programmer 122. The controller 154 can receive selections of, or adjustments to, neurostimulation parameter sets made by the patient via the user interface 152, and can transmit the selection or adjustment to the IPG 112 via telemetry circuitry 158. Where the patient programmer 126 stores data relating to neurostimulation parameter sets in the memory 159, the controller 154 can receive such data from the clinician programmer 122 via the input/output circuitry 156 during programming by a clinician or physician. Further, the patient programmer 126 can transmit data relating to neurostimulation parameter sets to the IPG 112 via the telemetry circuitry 158.

Figure 2:
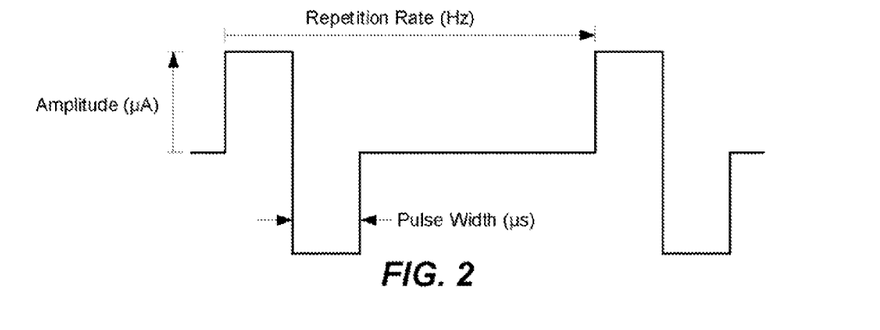
FIG. 2 illustrates possible variable parameters of a stimulation signal.

FIG. 2 illustrates possible parameters of a stimulation signal which may be varied. Using embodiments of the present invention, the amplitude, pulse width and repetition rate (also referred to as frequency) which provide the optimal therapeutic result can be determined, as will be described below.

Figure 3:
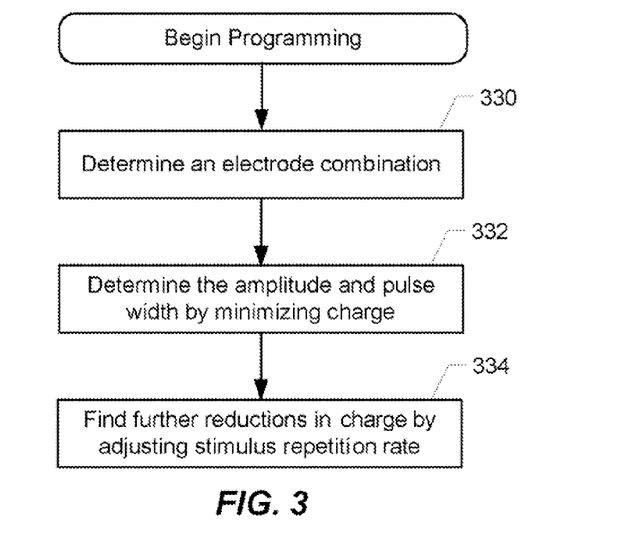
FIG. 3 illustrates a flowchart depicting a determination protocol of an embodiment the present invention.

Referring to FIG. 3, a high level flowchart depicting an example determination protocol of the present invention is provided. More specifically, the protocol shown in FIG. 3 can be used to identify, from among a plurality of possible neurostimulation parameter sets, one or more preferred neurostimulation parameter sets that treat a targeted pain of a patient, wherein each neurostimulation parameter set defines electrode parameters and neurostimulation signal parameters. Here, the protocol begins with step 330 comprising determining an electrode choice or an electrode combination. Next, step 332 comprises determining an amplitude and pulse width by minimizing charge. And further, step 334 comprises further reductions in charge by adjusting stimulus repetition rate. Each of these steps will be described in more detail herein.

Figure 4:
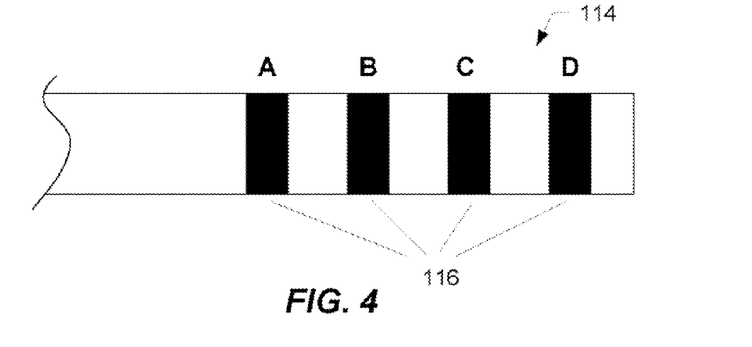
FIG. 4 illustrates a portion of an exemplary lead having four electrodes.

The electrode choice or the appropriate electrode combination can be determined based on the number of electrodes disposed on the lead and feedback from the patient. In some embodiments, a single electrode of a lead may be chosen and the IPG housing 113 or another electrode positioned remotely acts as a return electrode. In other embodiments, electrode pairs or combinations are determined wherein one electrode of a lead acts as the return electrode. For purposes of example, a lead 114 having four electrodes 116 (labeled A, B, C, D, as illustrated in FIG. 4) can be utilized and an electrode pair or combination can be determined. The electrode combination that provides the most desirable treatment result can be determined. Such an electrode combination may include electrodes that are closest to the target nerve tissue, such as the dorsal root ganglion, and/or the electrode combination that has the lowest stimulation threshold for target nerve activation can be determined. Additional details regarding stimulation of the dorsal root ganglion are provided in U.S. Pat. No. 7,450,993, entitled "Methods for Selective Stimulation of a Ganglion", which is incorporated herein by reference.

All possible combinations of electrodes can be tested, or only some of the possible combinations can be tested, e.g., the ones that a clinician or physician (or a system) identifies as most likely to have the best efficacy for the targeted pain. In this example, while more then eight combinations are possible, only the following eight possible electrode combinations are tested: AB, AC, AD, BC, BD, CD, ABC and BCD. However, more or less electrode combination can be tested. In this embodiment, while searching for the proper electrode combination, the repetition rate is held constant while the amplitude and pulse width are sequentially, but individually, altered. After each parameter change, the patient can be prompted by the external programmer 122 or 126, or by a clinician or physician, for feedback in order to determine efficacy. For example, the patient may receive the prompt, "Is the pain relieved?", in response to which the patient presses a button, or the like, on the external programmer 122 or 126 corresponding to YES or NO. For another example, the patient can be verbally prompted for feedback by, and can verbally provide their response to, a clinician or physician who can enter the response into the external programmer 122 or 126.

When a given electrode is selected to receive an electrical stimulus, it is (for purposes of the present invention) said to be "activated" or used to deliver neurostimulation. When an electrode is not selected to receive an electrical stimulus, it is said to be "non-activated" or not used to deliver neurostimulation. Electrical neurostimulation occurs between two or more electrodes so that the electrical current associated with the stimulus has a path from the IPG 112 to the tissue to be stimulated, and a return path from the tissue to the IPG 112. The electrically conductive housing 113 of the IPG 112 may function, in some modes of operation, as a return electrode, as mentioned above. Monopolar stimulation occurs when a selected one of the electrodes 116 of one of the leads 114 is activated along with the IPG housing 113 as the return electrode. Bipolar stimulation occurs when two of the electrodes of the leads 116 are activated, e.g., when one electrode 116 is activated as an anode at the same time that another electrode 116 is activated as a cathode. Tripolar stimulation occurs when three of the electrodes 116 of the lead(s) 114 are activated, e.g., two electrodes 116 can be activated as an anode at the same time that another electrode 116 is activated as a cathode. In general, multipolar stimulation occurs when multiple electrodes 116 of the lead(s) 114 are activated.

Figure 5:
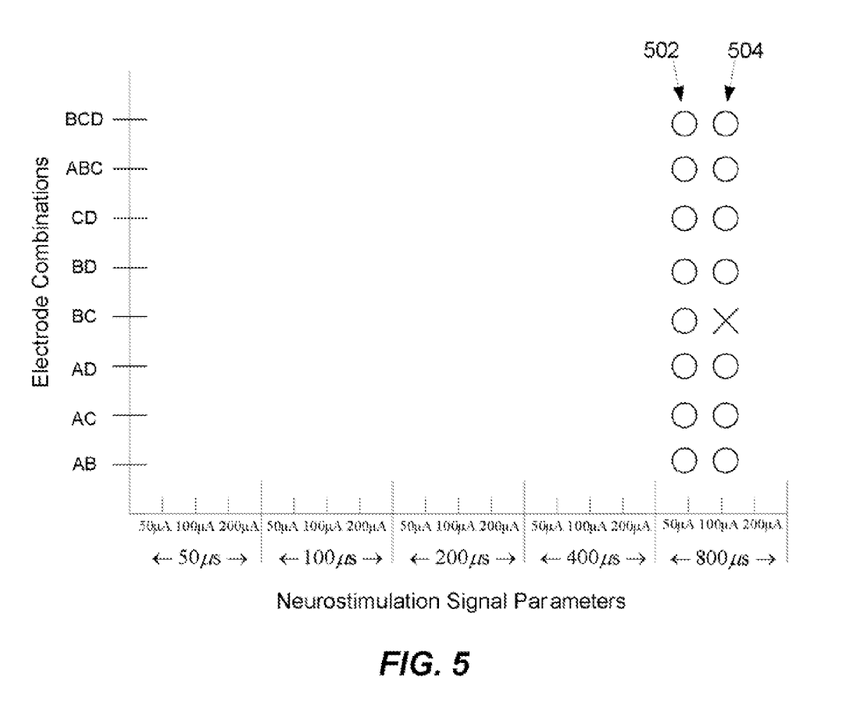
FIGS. 5 and 6 illustrate a scenario in which the optimal electrode pair is determined during a first tested pulse width combination.
Figure 6:
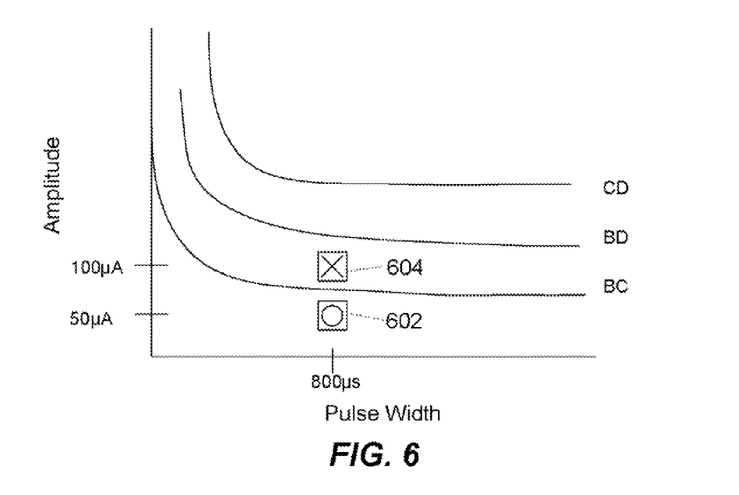

FIGS. 5 and 6 illustrate a scenario in which the optimal electrode combination (a pair in this example) is determined during the first tested pulse width combination. FIG. 5 provides electrode combinations along the y-axis (i.e., the vertical axis) and pulse width along the x-axis (i.e., the horizontal axis). Pulse amplitudes are also provided along the horizontal axis. Within each designated pulse width, the amplitude is varied. The pulse repetition rate is held constant. The protocol begins with neurostimulation signals sent to the electrode combinations in a sequence at a given pulse width (800 µs) and amplitude (50 µA). After each electrode combination is stimulated, the patient is prompted as to whether they experienced pain relief: "o" designating no pain relief and "x" designating pain relief. In this example, none of the electrode pair combinations provided pain relief at the given pulse width (800 µs) and amplitude (50 µA) as indicated by a column 502 of "o"s. The amplitude is then increased to the next designated amplitude (100 µA). In this example, the electrode pair BC provided pain relief as designated by an "x" in column 504 of FIG. 5.

FIG. 6 illustrates the theoretical threshold characteristics of the nerve tissue when stimulated by a designated electrode combination. Three threshold curves are shown, one for each electrode combination of BC, BD and CD. As pulse width increases, the threshold value decreases and becomes independent of the pulse width. Therefore the pulse width was initially set to 800 µs and the amplitude was set to 50 µA. As shown in FIG. 6, this stimulation setting was subthreshold for nerve activation, as indicated by the square 602 with an "o" in the center. When the stimulus amplitude was increased to 100 µA, the stimulation settings were above threshold for nerve activation with electrode configuration BC, as indicated by the square 604 with the "x" in the center.

Figure 7:
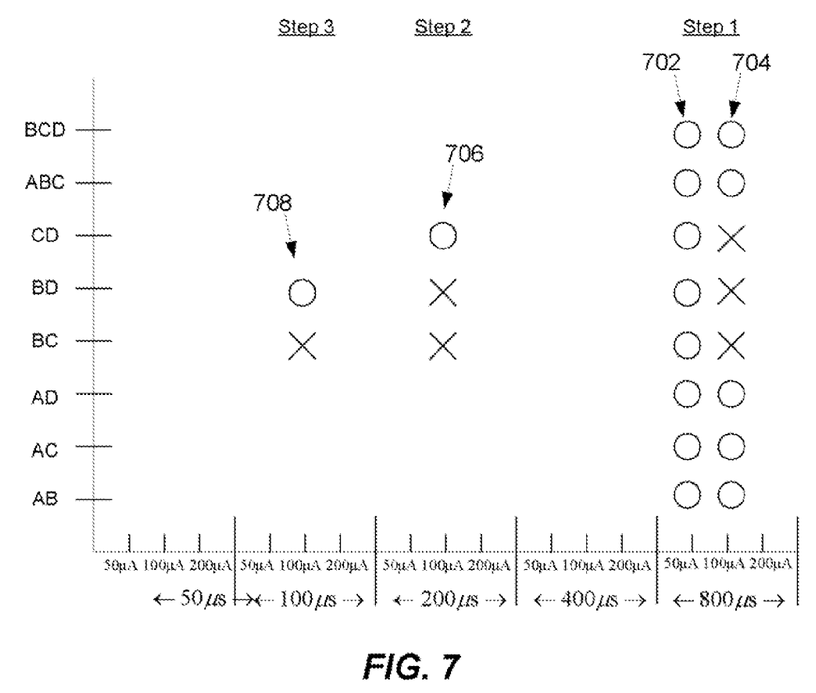
FIGS. 7 and 8 illustrate a scenario in which the optimal electrode pair is determined after three tested pulse width combinations.
Figure 8:
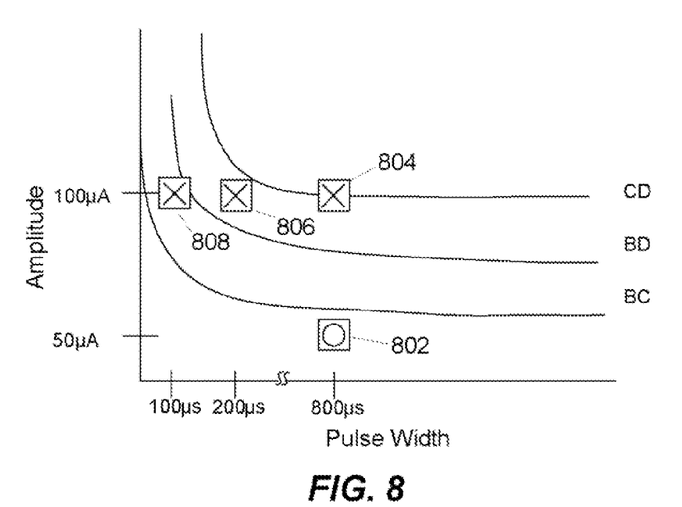

FIGS. 7 and 8 illustrate a scenario in which the optimal electrode combination (a pair in this example) is determined after three different pulse widths were tested. More specifically, a pulse width of 800 µs was tested with an amplitude of 50 µA and an amplitude of 100 µA, a pulse width of 200 µs was tested with an amplitude of 100 µA, and a pulse width of 100 µs was tested with an amplitude of 100 µA. FIG. 7 provides electrode combinations along the y-axis (i.e., vertical axis) and pulse width along the x-axis (i.e., horizontal axis). Pulse amplitudes are also provided along the horizontal axis. Within each designated pulse width, the amplitude can be varied. The repetition rate is held constant. The protocol begins with signals sent to the electrode pairs in a sequence at a given pulse width (800 µs) and amplitude (50 µA). After each electrode combination is stimulated, the patient is prompted as to whether they experienced pain relief: "o" designating no pain relief and "x" designating pain relief. In this example, none of the electrode pair combinations provided pain relief at the given pulse width (800 µs) and amplitude (50 µA) as indicated by a column 702 of "o"s. The amplitude is then increased to the next designated amplitude (100 µA). In this example, the electrode pairs BC, BD, CD provided pain relief as designated by "x"s in the column 704 in FIG. 7.

FIG. 8 illustrates the theoretical threshold characteristics of the nerve tissue when stimulated by a designated electrode combination. Three threshold curves are shown, one for each electrode combination of BC, BD and CD. As shown, the pulse width was initially set to 800 μs and the amplitude was set to 50 μA. This stimulation setting was subthreshold for nerve activation, as indicated by the square 802 with an "o" in the center. When the stimulus amplitude was increased to 100 μA, the stimulation settings were above threshold for nerve activation with electrode configurations BC, BD and CD as indicated by the right-most square 804 with the "x" in the center. In this example, the threshold characteristics of all three electrode combinations are similar and the differences in their rheobase currents are less than the incremental increase in amplitude (50 μA graduations, in this example).

Referring again to FIG. 7, the testing was then repeated with the amplitude maintained 100 μA and the pulse width lowered to 200 μs. In an embodiment, the step size of the decrease in pulse width is proportional to the number of electrode combinations that resulted in patient pain relief (e.g. if two electrode pairs were successful in producing pain relief, the step size would be much smaller than if six electrode combinations produced pain relief). Still referring to FIG. 7, the electrode pairs BC and BD provided pain relief at the reduced amplitude as designated by "x"s in the center column 706 of FIG. 7. Referring back to FIG. 8, the stimulation setting was subthreshold for nerve activation of electrode configuration CD, but still above threshold for electrode configurations BC and BD as indicated by the square 806 with the "x" in the center.

The testing was then repeated with the amplitude maintained 100 μA and the pulse width lowered to 100 μs. Referring to FIG. 7, the electrode pair BC provided pain relief at the further reduced amplitude as designated by an "x" in the column 708 on the left side of FIG. 7. Referring back to FIG. 8, the stimulation setting was subthreshold for nerve activation of electrode configurations BD, CD, but still above threshold for electrode configuration BC as indicated by the left-most square 808 with the "x". As was indicated above in the discussion of step 334 of FIG. 3, further reductions in charge can be tested by adjusting (e.g., reducing) the repetition rate, to attempt to conserve power.

In this example, the external programmer 122 (or 126) was able to determine the optimal electrode configuration, pulse width, amplitude and repetition rate for a given patient based on periodic feedback inputs from the patient. The IPG 112 is then programmed with these parameters to provide optimal treatment for the patient.

Figure 9:
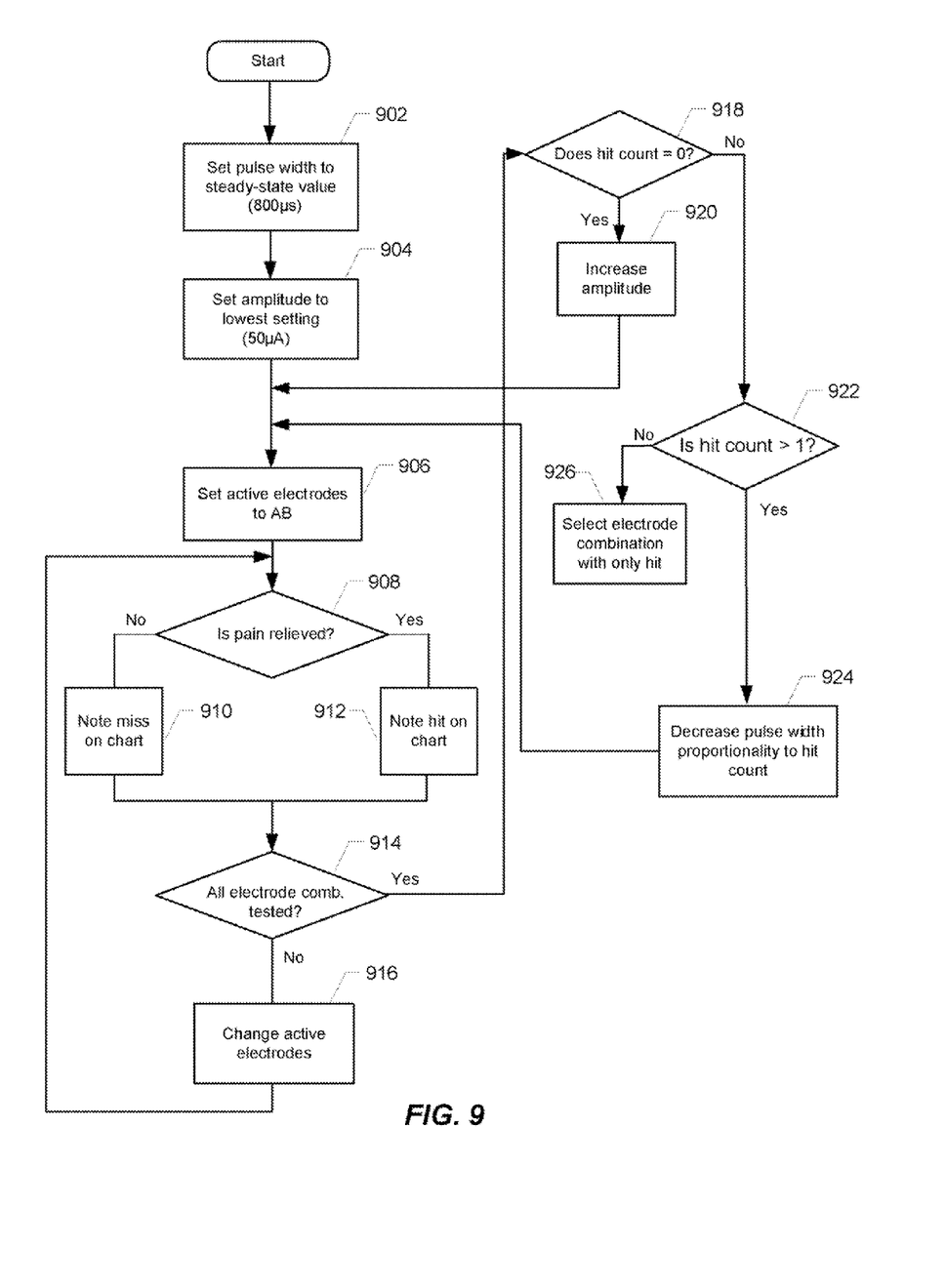
FIG. 9 provides a more detailed flowchart of example determinations made by an external programmer, in accordance with an embodiment of the present invention.

FIG. 9 provides a more detailed flowchart of example determinations made by the external programmer 122 (or 126) during execution of the code modules to determine the neurostimulation parameters, in accordance with an embodiment of the present invention. This flowchart reflects the example described above in relation to FIGS. 7 and 8. The various steps or blocks in the flow chart are used to summarize algorithmic steps. Such steps or blocks describe specific actions or decisions that are made or carried out as the algorithm proceeds. Where a controller (or equivalent) is employed, the flowchart presented herein provides the basis for a 'control program' that may be used by such a controller (or equivalent) to effectuate the desired control of the system. Those skilled in the art may readily write such a control program based on the flowchart and other descriptions presented herein.

Referring to FIG. 9, at step 902 the pulse width of the neurostimulation signal is set to a steady state value (e.g., 800 μs). At step 904 the amplitude of the neurostimulation signal is set to an initial setting (e.g., 50 μA), which may be its lowest setting. At step 906, one of the possible electrode combinations is selected and set up (e.g., pair AB). At this point, a neurostimulation parameter set is tested to determine at step 908 whether the patient's targeted pain is relieved using the tested neurostimulation parameter set, where the neurostimulation parameter set defines electrode parameters and neurostimulation signal parameters. The electrode parameters of a neurostimulation parameter set can define which electrodes are used to provide neurostimulation. Additionally, the electrode parameters of a neurostimulation parameter set can define which electrode(s) used to provide neurostimulation are connected as a cathode, and which electrode(s) used to provide neurostimulation are connected as an anode. The neurostimulation signal parameters of a neurostimulation parameter set can define a value for each of pulse width, pulse amplitude and pulse repetition rate.

If the pain is not relieved, then at step 910 a miss is noted in a chart, e.g., which can be stored as a look up table (LUT), or the like. If the pain is relieved, then at step 912 a hit is noted in the chart. A graphical representation of such a chart was described above with reference to FIG. 7.

Still referring to FIG. 9, at step 914 there is a determination of whether all of the electrode combinations to be tested have been tested. In other words, there is a determination of whether there are more electrode combinations to test using the presently defined neurostimulation signal parameters. If there is another electrode combination to test, then the electrode combination is changed at step 916, and steps 908-912 are repeated for one or more additional electrode combinations. More generally, steps 906-916 are repeated until there is a determination at step 914 that there are no more electrode combinations to test the using the presently defined neurostimulation signal parameters.

When there is a determination at step 914 that there are no more electrode combinations to test the using the presently defined neurostimulation signal parameters, there is a determination at step 918 whether a hit count equals zero. In other words, at step 918 there is a determination of whether any of the electrode combinations tested successful relieved that patient's targeted pain at the increased amplitude. If no electrode combination was successful, then at step 920 the pulse amplitude is increased. Thereafter, steps 906-916 are repeated using the increased pulse amplitude, in an attempt to identify at least one electrode combination that will successfully treat the patient's targeted pain. As can be appreciated from FIG. 9, the pulse amplitude can be increased as many times as necessary.

Referring again to step 918, when the hit count is not equal to zero, i.e., when at least one of the tested electrode combinations successful relieved that patient's targeted pain, then flow goes to step 922. At step 922 there is a determination of whether the hit count is greater than one. In other words, at step 922 there is a determination of whether more than one of the tested electrode combinations successful relieved that patient's targeted pain. If it is determined at step 922 that only one tested electrode combination successfully relieved that patient's targeted pain, then that electrode combination is selected at step 926 as being the electrode parameters for the preferred neurostimulation parameter set, along with the corresponding neurostimulation signal parameters (e.g., pulse width, pulse amplitude and pulse repetition rate, but not limited thereto). If it is determined at step 922 that more than one tested electrode combination successfully relieved that patient's targeted pain (i.e., if the hit count is greater than zero), then the protocol continues in an attempt to narrow down the selection to a single preferred neurostimulation parameter set. In accordance with an embodiment, such narrowing down is performed in a manner that reduces power consumption, since the lower the power consumption the greater the longevity of the battery of the IPG. More specifically, as indicated at step 924, the pulse width neurostimulation signal parameter is reduced, and then steps 906-916 are repeated at the reduced pulse width. In accordance with an embodiment, the amount by which the pulse width is reduced at step 924 is proportional to the hit count for the most recently tested pulse width. More generally, the greater hit count the greater the amount by which the pulse width is reduced.

As steps 906-924 are repeated, the amplitude can be incrementally increased (at step 920) and the pulse width can be incrementally decreased (at step 924) as necessary, until only a single neurostimulation parameter set is identified and selected.

The steps of FIG. 9 can be performed by or with the assistance of portions of the system 110 described above. For example, various steps can be performed by or with the assistance of the external programmer(s) 122 and/or 126, the IPG 112, the leads 114 and the electrodes 116. In one embodiment, the steps (with the exception of step 908) are performed automatically by an external patient programmer (122 or 126), and step 908 is performed in response to feedback via a user interface (142 or 152) from the patient.

Once the appropriate electrode choice or electrode combination is determined, the optimal pulse width, amplitude and repetition rate can be determined using a similar protocol to that described in relation to FIGS. 5-9. For example, in a similar manner as described above, further neurostimulation signal parameters, such as pulse width and repetition rate can be incrementally adjusted to determine optimal parameters. For example, once an electrode combination is selected, and an amplitude is selected, the pulse width and/or repetition rate can be incrementally reduced to determine if the targeted pain would still be treated at a reduced pulse width and/or repetition rate, which would conserve power. In an embodiment, the amplitude can be set to a steady state, and a protocol similar to that shown in FIG. 9 can be used to adjust pulse width to select an optimal pulse width at the steady state amplitude. In another embodiment, the amplitude and pulse width can be set to a steady state, and a protocol similar to that shown in FIG. 9 can be used to adjust repetition rate to select an optimal repetition rate at the steady state amplitude and pulse width. It is also possible that such protocols can be used one after the other to fine tune all of the various parameters, or identify multiple neurostimulation parameter sets that treat the targeted pain. Where multiple neurostimulation parameter sets are identified, a patient can be allowed to select amount the various neurostimulation parameter sets, and/or a most power efficient neurostimulation parameter set can be selected.

Embodiments of the present invention have been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the claimed invention.

Although the foregoing invention has been described in some detail by way of illustration and example, for purposes of clarity and understanding, it will be obvious that various alternatives, modifications and equivalents may be used and the above description should not be taken as limiting in scope of the invention

What is claimed is:

1. A method for efficiently identifying, from among a plurality of possible neurostimulation parameter sets, one or more preferred neurostimulation parameter sets that treat a targeted pain of a patient, wherein each neurostimulation parameter set defines electrode parameters and neurostimulation signal parameters, the method comprising:
   (a) testing on the patient a plurality of different neurostimulation parameter sets to thereby identify those tested neurostimulation parameter sets that treat the targeted pain,
      wherein each of the tested neurostimulation parameter sets defines an electrode configuration that differs from the other tested neurostimulation parameter sets, and
      wherein all of the tested neurostimulation parameter sets comprise a same value for a specific neurostimulation signal parameter that if reduced reduces power consumption; and
   (b) retesting on the patient the neurostimulation parameter sets identified as treating the targeted pain, with the value for the specific neurostimulation signal parameter reduced by a same amount for each of the retested neurostimulation parameter sets, to thereby identify those neurostimulation parameter sets that treat the targeted pain at the reduced power consumption level;
      wherein at step (b), the amount by which the value of the specific neurostimulation signal parameter is reduced for each of the retested neurostimulation parameter sets is dependent upon the number of neurostimulation parameter sets being retested, such that the greater the number of neurostimulation parameter sets being retested the greater the amount by which the value of the specific neurostimulation signal parameter is reduced.

2. The method of claim 1, wherein if more than one neurostimulation parameter set that treats the targeted pain is identified at step (b), then repeating step (b) until only one neurostimulation parameter set that treats the targeted pain is identified, wherein each time step (b) is repeated the value for the specific neurostimulation signal parameter is again reduced.

3. The method of claim 2, wherein each time step (b) is repeated, the amount by which the value for the specific neurostimulation signal parameter is reduced stays the same if the number of neurostimulation parameter sets being retested stays the same, or decreases if the number of neurostimulation parameter sets being retested decreases.

4. The method of claim 1, wherein at step (b), the amount by which the value of the specific neurostimulation signal parameter is reduced for each of the retested neurostimulation parameter sets is proportional to the number of neurostimulation parameter sets being retested.

5. The method of claim 1, wherein the specific neurostimulation signal parameter comprises pulse width.

6. The method of claim 1, wherein the specific neurostimulation signal parameter comprises pulse amplitude.

7. The method of claim 1, wherein the specific neurostimulation signal parameter comprises pulse repetition rate.

8. The method of claim 1, wherein the electrode parameters of each neurostimulation parameter set define which electrodes are used to provide neurostimulation.

9. The method of claim 8, wherein the electrode parameters of each neurostimulation parameter set define which one or more electrodes used to provide neurostimulation are connected as a cathode, and which one or more electrodes used to provide neurostimulation are connected as an anode.

10. The method of claim 1, wherein neurostimulation signal parameters of each neurostimulation parameter set define a value for each of pulse width, pulse amplitude and pulse repetition rate.

11. The method of claim 1, wherein if none of the neurostimulation parameter sets tested at step (a) treat the targeted pain, then prior to step (b), retesting on the patient the plurality of neurostimulation parameter sets with a value for the specific neurostimulation signal parameter or another neurostimulation parameter increased by a same amount for each of the retested neurostimulation parameter sets, to thereby identify those neurostimulation parameter sets that treat the targeted pain with the increased value.

12. The method of claim 1, wherein:
the plurality of neurostimulation parameter sets comprise dorsal root ganglion (DRG) neurostimulation parameter sets for DRG stimulation of the patient;
step (a) comprises testing on the patient the plurality of different DRG neurostimulation parameter sets to thereby identify those tested DRG neurostimulation parameter sets that treat the targeted pain; and
step (b) comprises retesting on the patient the DRG neurostimulation parameter sets identified as treating the targeted pain, with the value for the specific DRG neurostimulation signal parameter reduced by a same amount for each of the retested neurostimulation parameter sets, to thereby identify those DRG neurostimulation parameter sets that treat the targeted pain at the reduced power consumption level.

13. An external programmer configured to efficiently identify, from among a plurality of possible neurostimulation parameter sets, one or more preferred neurostimulation parameter sets that treat a targeted pain of a patient, wherein each neurostimulation parameter set defines electrode parameters and neurostimulation signal parameters, the external programmer including:
memory to store a plurality of different neurostimulation parameter sets to be tested on the patient, wherein all of the neurostimulation parameter sets to be tested comprise a same value for a specific neurostimulation signal parameter that if reduced reduces power consumption;
a controller configured to provide test instructions that instruct an implantable pulse generator (IPG), implanted within the patient, to test on the patient the plurality of different neurostimulation parameter sets;
telemetry circuitry configured to transmit the test instructions to the IPG implanted within the patient; and
a user interface configured to accept feedback that identifies those tested neurostimulation parameter sets that treat the targeted pain;
wherein the controller is also configured to provide retest instructions, in response to more than one of the tested neurostimulation parameter sets being identified as treating the targeted pain, wherein the retest instructions instruct the IPG to retest on the patient the neurostimulation parameter sets identified as treating the targeted pain, with the value for the specific neurostimulation signal parameter reduced by a same amount for each of the retested neurostimulation parameter sets;
wherein the amount by which the value of the specific neurostimulation signal parameter is reduced for each of the retested neurostimulation parameter sets is dependent upon the number of neurostimulation parameter sets being retested, such that the greater the number of neurostimulation parameter sets being retested the greater the amount by which the value of the specific neurostimulation signal parameter is reduced;
wherein the telemetry circuit is also configured to transmit the retest instructions to the IPG; and
wherein the user interface is also configured to accept feedback that identifies those retested neurostimulation parameter sets that treat the targeted pain at the reduced power consumption level.

14. The external programmer of claim 13, wherein the external programmer comprises a patient programmer.

15. The external programmer of claim 13, wherein the external programmer comprises a clinician programmer.

16. The external programmer of claim 13, wherein the controller is configured to repeatedly provide retest instructions, in response to more than one of the retested neurostimulation parameter sets being identified as treating the targeted pain, wherein each time the controller provides retest instructions, the value for the specific neurostimulation signal parameter is again reduced.

17. The external programmer of claim 16, wherein each time the controller provides retest instructions, the amount by which the value for the specific neurostimulation signal parameter is reduced stays the same if the number of neurostimulation parameter sets being retested stays the same, or decreases if the number of neurostimulation parameter sets being retested decreases.

18. The external programmer of claim 16, wherein each time the controller provides retest instructions, the amount by which the value of the specific neurostimulation signal parameter is reduced is proportional to the number of neurostimulation parameter sets being retested.

19. The external programmer of claim 13, wherein the specific neurostimulation signal parameter comprises pulse width.

20. The external programmer of claim 13, wherein the specific neurostimulation signal parameter comprises pulse amplitude.

21. The external programmer of claim 13, wherein the specific neurostimulation signal parameter comprises pulse repetition rate.

22. The external programmer of claim 13, wherein the electrode parameters of each neurostimulation parameter set define which electrodes are used to provide neurostimulation.

23. The external programmer of claim 13, wherein the electrode parameters of each neurostimulation parameter set define which one or more electrodes used to provide neurostimulation are connected as a cathode, and which one or more electrodes used to provide neurostimulation are connected as an anode.

24. The external programmer of claim 13, wherein neurostimulation signal parameters of each neurostimulation parameter set define a value for each of pulse width, pulse amplitude and pulse repetition rate.

25. The external programmer of claim 13, wherein the controller is configured to provide retest instructions, in response to none of the tested neurostimulation parameter sets being identified as treating the targeted pain, wherein the retest instructions instruct the IPG to retest on the patient the plurality of neurostimulation parameter sets, with a value for the specific neurostimulation signal parameter or another neurostimulation signal parameter increased by a same amount for each of the retested neurostimulation parameter sets.

26. The external programmer of claim 13, wherein the plurality of neurostimulation parameter sets comprise dorsal root ganglion (DRG) neurostimulation parameter sets for DRG stimulation of the patient.

* * * * *